United States Patent
Aiba et al.

(10) Patent No.: US 12,213,849 B2
(45) Date of Patent: Feb. 4, 2025

(54) DENTAL ZIRCONIA BLANK HAVING MULTILAYER STRUCTURE DIFFERENT IN CONTENT OF YTTRIA

(71) Applicant: SHOFU INC., Kyoto (JP)

(72) Inventors: Rieko Aiba, Kyoto (JP); Shuhei Takahashi, Kyoto (JP); Toshio Kitamura, Kyoto (JP)

(73) Assignee: SHOFU INC., Kyoto (JP)

( * ) Notice: Subject to any disclaimer, the term of this patent is extended or adjusted under 35 U.S.C. 154(b) by 874 days.

(21) Appl. No.: 16/357,373

(22) Filed: Mar. 19, 2019

(65) Prior Publication Data

US 2019/0380815 A1 Dec. 19, 2019

(30) Foreign Application Priority Data

Mar. 20, 2018 (JP) .................. 2018-052050
Mar. 15, 2019 (JP) .................. 2019-048083

(51) Int. Cl.
*A61C 13/00* (2006.01)
*C04B 35/486* (2006.01)

(52) U.S. Cl.
CPC ........ *A61C 13/0022* (2013.01); *C04B 35/486* (2013.01); *C04B 2235/3225* (2013.01);
(Continued)

(58) Field of Classification Search
None
See application file for complete search history.

(56) References Cited

U.S. PATENT DOCUMENTS

2013/0224454 A1* 8/2013 Jung ................ B32B 18/00
264/16
2015/0282905 A1* 10/2015 Jahns ................ B82Y 30/00
433/167
(Continued)

FOREIGN PATENT DOCUMENTS

CN 106660885 5/2017
EP 3 108 849 12/2016
(Continued)

OTHER PUBLICATIONS

Extended European Search Report issued Oct. 15, 2019 in corresponding European Patent Application No. 19163843.6.
(Continued)

*Primary Examiner* — Mohammad M Ameen
(74) *Attorney, Agent, or Firm* — WENDEROTH, LIND & PONACK, L.L.P.

(57) ABSTRACT

To provide a dental zirconia blank which has high permeability, can reproduce a color tone close to a natural tooth and a strength to be able to tolerate in oral cavity. Furthermore, to provide a dental zirconia blank from which a prosthesis device of 4 or more units having high strength can be prepared. To provide a dental zirconia blank having a plurality of layers, comprising; a first layer consisting of a high permeability ceramic containing 91.6 to 96.5 mol % of zirconium oxide and 3.5 to 8.4 mol % of yttrium oxide, and a second layer consisting of a low permeability ceramic containing 95.6 to 98.5 mol % of zirconium oxide and 1.5 to 4.4 mol % of yttrium oxide, wherein a content rate of yttrium oxide in the low permeability ceramic is lower than a content rate of yttrium oxide in the high permeability ceramic by 0.5 to 5.4 mol %, and the first layer is positioned at one end of the plurality of layers in a layering direction.

17 Claims, 1 Drawing Sheet

(52) U.S. Cl.
CPC ............... *C04B 2235/3244* (2013.01); *C04B 2235/9653* (2013.01)

(56) References Cited

U.S. PATENT DOCUMENTS

| | | |
|---|---|---|
| 2016/0310245 A1 | 10/2016 | Fujisaki et al. |
| 2017/0143458 A1 | 5/2017 | Fujisaki et al. |
| 2017/0273764 A1* | 9/2017 | Volkl ..................... A61K 6/15 |

FOREIGN PATENT DOCUMENTS

| | | |
|---|---|---|
| EP | 3 108 849 A1 * | 12/2016 |
| JP | 2015-143178 | 8/2015 |
| KR | 10-1601948 | 3/2016 |
| WO | 2017/162571 | 9/2017 |

OTHER PUBLICATIONS

Japanese Office Action issued Sep. 20, 2022 in corresponding Japanese Patent Application No. 2019-048083, with English translation.

Chinese Office Action issued Mar. 2, 2022 in corresponding Chinese Patent Application No. 201910208687.0, with English translation.

\* cited by examiner

DENTAL ZIRCONIA BLANK HAVING MULTILAYER STRUCTURE DIFFERENT IN CONTENT OF YTTRIA

CROSS-REFERENCE TO RELATED APPLICATIONS

This application is based on and claims the benefit of priorities from Japanese Patent Application Serial No. 2018-052050 (filed on Mar. 20, 2018) and Japanese Patent Application Serial No. 2019-048083 (filed on Mar. 15, 2019), the contents of which are hereby incorporated by reference in their entirety.

BACKGROUND OF THE INVENTION

Field of the Invention

The present disclosure relates to a dental zirconia blank used for cutting and machining for CAD/CAM applications in a dental field.

Description of the Related Art

In the conventional dental treatment of a defect part of a dental crown, a prosthetic restoration using a casting crown bridge and an artificial tooth has been performed generally. Specific examples include a clinical application of a porcelain baked crown bridge which reproduces a tooth crown shape by baking porcelain on a surface of a metal frame made from a casting alloy for porcelain baking and has a functionality and aesthetic property.

In addition, from the point of view of the metal allergy and the price remarkable rise to depend on the noble metal market price and from the point of view of aesthetic property which can imitate the color tone of the natural tooth, a prosthesis device, which is so-called all ceramics, prepared by the dipping method using such as alumina, aluminosilicate glass, lithium disilicate glass or by the press method using ceramic ingot, has attracted attention, and, the prosthesis restoration using it has been increased.

In recent years, techniques to prepare a prosthesis device by the cutting and machining which uses a dental CAD/CAM system spread rapidly and it has been becoming possible to easily prepare prosthetic devices by milling the blanks such as a block and a disk which are made of zirconia, alumina, aluminosilicate glass, and lithium disilicate glass. In addition, although zirconia is frequently used in the clinical as high-strength ceramics, a zirconia blank (pre-sintered body) which has adjusted strength and hardness which are advantageous for cutting and machining and is prepared by pre-sintering (temporary calcined) at low sintering temperature is generally used. The zirconia blank is not subjected to the perfect sintering in order to improve cutting property in zirconia.

Among such zirconia blanks, a zirconia blank containing 3 mol % of yttrium oxide has been put to practical use because of having the bending strength which is used in the frame of 4 or more unit bridge. This zirconia blank containing 3 mol % of yttrium oxide is added with a very small amount of alumina for improving sinterability and restraining the low temperature deterioration.

However, it is difficult for the zirconia blank containing 3 to 4 mol % of yttrium oxide to reproduce transparency corresponding to the enamel portion of a tooth. Therefore it is necessary to build a glass which is called as the porcelain to enamel. However, this process is a very complicated process and requires the technique of the technician.

In recent year, in order to increase optical transparency and to use as a molar tooth full crown, a zirconia blank prepared from zirconia powder in which alumina content is controlled to an infinitesimal has been clinically used. In addition, in order to use as a front tooth full crown in which aesthetic property is more required, a zirconia blank in which optical transparency is highly designed by increasing the content of yttrium oxide which is added as a stabilizer to 5-6 mol % also has been used.

Japanese Examined Patent Application Publication No. 2015-143178 discloses that a zirconia sintered body containing yttrium oxide within a range of 4.0 mol % to 6.5 mol % has total light transmittance within a range of 37% to less than 40% and has translucency and strength particularly suitable to a front tooth. It is described that translucency is high and bending strength is 500 MPa or more.

However, although it can be said that the bending strength of 500 MPa is enough strength in a single crown, it cannot be said that the bending strength of 500 MPa is enough strength in the case of the prosthesis device of the plural units such as bridge. Particularly, because large power is applied to a connecting portion by an occlusion, higher bending strength is required.

SUMMARY OF THE INVENTION

Technical Problem

By using the conventional zirconia powder, although optical transparency and aesthetic property are improved, strength is decreased. When the strength is decreased, the applicable case is limited, and a risk that a prosthetic device is broken in oral cavity is concerned.

An object of the present disclosure is to provide a dental zirconia blank which has high permeability, can reproduce a color tone close to a natural tooth and a strength to be able to tolerate in oral cavity. Furthermore, other object of the present disclosure is to provide a dental zirconia blank from which a prosthesis device of 4 or more units having high strength can be prepared.

Solution to Problem

The present disclosure provides a dental zirconia blank having a plurality of layers, comprising; a first layer consisting of a high permeability ceramic containing 91.6 to 96.5 mol % of zirconium oxide and 3.5 to 8.4 mol % of yttrium oxide, and a second layer consisting of a low permeability ceramic containing 95.6 to 98.5 mol % of zirconium oxide and 1.5 to 4.4 mol % of yttrium oxide, wherein a content rate of yttrium oxide in the low permeability ceramic is lower than a content rate of yttrium oxide in the high permeability ceramic by 0.5 to 5.4 mol %, and the first layer is positioned at one end of the plurality of layers in a layering direction.

In the present disclosure, it is preferable that the first layer consists of a plurality of high permeability layered areas having different compositions with each other.

In the present disclosure, it is preferable that the first layer comprises a plurality of high permeability layered areas having different content rates of zirconium oxide and/or different content rates of yttrium oxide in high permeability ceramic with each other.

In the present disclosure, it is preferable that at least one high permeability layered area includes 0.0001 to 0.30 mol % of erbium oxide.

In the present disclosure, it is preferable that the second layer consists of a plurality of low permeability layered areas having different compositions with each other.

In the present disclosure, it is preferable that the second layer comprises a plurality of low permeability layered areas having different content rates of zirconium oxide and/or different content rates of yttrium oxide in the low permeability ceramic with each other.

In the present disclosure, it is preferable that at least one low permeability layered area includes 0.0001 to 0.30 mol % of erbium oxide.

In the present disclosure, it is preferable that the high permeability ceramic is a temporary calcined body of a plurality of powders having different compositions with each other.

In the present disclosure, it is preferable that the low permeability ceramic is a temporary calcined body of a plurality of powders having different compositions with each other.

In the present disclosure, it is preferable that the first layer is positioned to a position spaced from a surface of a side of the one end by a range of 5 to 40% of a dimension between the surface of the side of the one end and a surface of a side of the other end opposing to the surface of the side of the one end on a perpendicular line from the center of the gravity of the surface of the side of the one end at which the first layer is positioned in the layering direction of the dental zirconia blank.

In the present disclosure, it is preferable that a difference of BET specific surface area between a ceramic powder constituting the high permeability ceramic and a ceramic powder constituting the low permeability ceramic is within a range of 2 m$^2$/g and a difference of an average primary particle diameter between the ceramic powder constituting the high permeability ceramic and the ceramic powder constituting the low permeability ceramic is within a range of 20 nm.

In the present disclosure, it is preferable that transparency of at least one high permeability layered area is higher than transparency of the second layer, and the chromaticities LE, aE, bE of the at least one high permeability layered area based on the L*·a*·b* colorimetric system satisfy the following relations: $65.0 \leq LE \leq 82.0$, $-4.0 \leq aE \leq 2.0$ and $0.0 \leq bE \leq 20.0$.

In the present disclosure, it is preferable that transparency of the first layer is higher than transparency of the second layer, and the chromaticities LE, aE, bE of the first layer based on the L*·a*·b* colorimetric system satisfy the following relations:

$$65.0 \leq LE \leq 82.0, -4.0 \leq aE \leq 2.0 \text{ and } 0.0 \leq bE \leq 20.0.$$

In the present disclosure, it is preferable that the first layer includes 0.0001 to 0.30 mol % of erbium oxide.

In the present disclosure, it is preferable that the second layer includes 0.0001 to 0.30 mol % of erbium oxide.

In the present disclosure, it is preferable that the high permeability ceramic consists of zirconium oxide and yttrium oxide.

In the present disclosure, it is preferable that the low permeability ceramic consists of zirconium oxide and yttrium oxide.

In the present disclosure, it is preferable that the first layer consists of high permeability ceramic.

In the present disclosure, it is preferable that the second layer consists of high permeability ceramic.

In the present disclosure, it is preferable that the dental zirconia blank consists of the first layer and the second layer.

Figure 1:
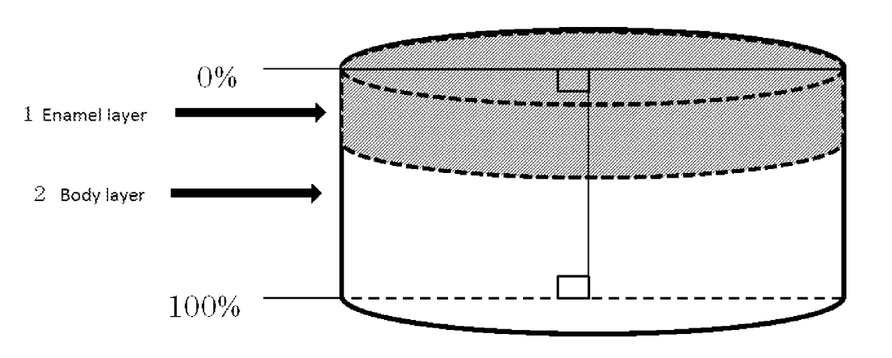
FIG. 1 shows an image drawing of the dental zirconia blank and an auxiliary line indicating an imaginary perpendicular line is illustrated.

The perpendicular line from the center of the gravity in the present specification is shown in FIG. 1, for example.

Advantageous Effects of Invention

The present disclosure provides a zirconia prosthesis device which can be cut and machined with CAD/CAM technique and exhibits high permeability and high strength after sintering. It is possible to use in various clinical case because applicable clinical case is not limited and to reproduce a color tone close to a natural tooth by multicolor multilayer structure.

DETAILED DESCRIPTION OF THE PREFERRED EMBODIMENTS

The dental zirconia blank of the present disclosure has a plurality of layers, more specifically, comprises a first layer positioned at one end in a layering direction of the plurality of layers and a second layer. The first layer and the second layer do not indicate the order thereof. It is preferable that the first layer corresponds to an enamel layer and the second layer corresponds to a body layer.

The first layer consists of a high permeability ceramic containing 91.6 to 96.5 mol % of zirconium oxide and 3.5 to 8.4 mol % of yttrium oxide.

When the content of the yttrium oxide in the high permeability ceramic is less than 3.5 mol %, it is difficult to reproduce an enamel layer. In addition, when the content of the yttrium oxide in the high permeability ceramic is more than 8.5 mol %, it is difficult to obtain sufficient bending strength. The content of the yttrium oxide in the high permeability ceramic is preferably within a range of 4.0 to 8.0 mol %, most preferably within a range of 4.5 to 6.5 mol %. Permeability is increased and sufficient bending strength is achieved by such a content.

The second layer consists of a low permeability ceramic containing 95.6 to 98.5 mol % of zirconium oxide and 1.5 to 4.4 mol % of yttrium oxide.

When the content of the yttrium oxide in the low permeability ceramic is less than 1.5 mol %, a sintered body is destroyed. In addition, when the content of the yttrium oxide in the low permeability ceramic is more than 4.4 mol %, a background color is reflected even if coloring is applied. The content of the yttrium oxide in the low permeability ceramic is preferably within a range of 2.0 to 4.0 mol %, most preferably within a range of 2.5 to 3.5 mol %. It is hard to be influenced by a background color and sufficient bending strength is achieved by such a content.

The content rate of yttrium oxide in the low permeability ceramic is lower than a content rate of yttrium oxide in the high permeability ceramic by 0.5 to 5.4 mol %. When the difference of the content rate of the yttrium oxide is less than 0.4 mol %, there is a case where an effect of improvement of aesthetic property by having a plurality of layers is not recognized. On the other hand, when the difference of the content rate of the yttrium oxide is more than 5.4 mol %, aesthetic property is impaired. The difference of the content rate of the yttrium oxide between the first layer and the second layer is preferably within a range of 0.5 to 4.0 mol % and most preferably within a range of 0.5 to 3.0 mol %. A gradation having more natural permeability is achieved to increase aesthetic property by such a content.

The first layer may consist of a plurality of high permeability layered areas having different compositions with each other. For example, the first layer may comprise a plurality of high permeability layered areas having different content rates of zirconium oxide and/or different content rates of yttrium oxide in high permeability ceramic with each other. By such a constitution, an effect of forming a gradation of color tone and/or permeability to prepare a prosthesis device more close to a natural tooth is obtained.

In this case, it is preferable that at least one high permeability layered area contained in the first layer includes 0.0001 to 0.30 mol % of erbium oxide. When at least one high permeability layered area contains the erbium oxide, a solid solving occurs to obtain an effect of a suppression of a color skip caused by sintering and an effect of reddish coloring. When the content of the erbium oxide is less than 0.0001 mol %, it is difficult to obtain such effects. On the other hand, when the content of the erbium oxide is more than 0.30 mol %, there is a case where a problem that a reddish becomes too strong and therefore it is not suitable as a tooth crown color is caused.

The second layer may consist of a plurality of low permeability layered areas having different compositions with each other. For example, the second layer may comprise a plurality of low permeability layered areas having different content rates of zirconium oxide and/or different content rates of yttrium oxide in the low permeability ceramic with each other. By such a constitution, an effect of forming a gradation of color tone and/or permeability to prepare a prosthesis device more close to a natural tooth is obtained.

In this case, it is preferable that at least one low permeability layered area contained in the second layer includes 0.0001 to 0.30 mol % of erbium oxide. When at least one low permeability layered area contains the erbium oxide, a solid solving occurs to obtain an effect of a suppression of a color skip caused by sintering and an effect of reddish coloring. When the content of the erbium oxide is less than 0.0001 mol %, it is difficult to obtain such effects. On the other hand, when the content of the erbium oxide is more than 0.30 mol %, there is a case where a problem that a reddish becomes too strong and therefore it is not suitable as a tooth crown color is caused.

The high permeability ceramic may be a temporary calcined body of a plurality of powders having different compositions with each other. By such a constitution, an effect that a prosthesis device having difference color tones and/or permeabilities is easily prepared by forming a tooth shape by cutting and machining with CAD/CAM technique, and by sintering it. In this case, a plurality of ceramic powders may constitute a plurality of high permeability layered areas and single high permeability layered area. In the case of plural, color tone reproduce property is excellent. In the case of single, productivity is excellent and the color tone can be reproduced.

The low permeability ceramic may be a temporary calcined body of a plurality of powders having different compositions with each other. By such a constitution, an effect that a prosthesis device having difference color tones and/or permeabilities is easily prepared by forming a tooth shape by cutting and machining with CAD/CAM technique, and by sintering it. In this case, a plurality of ceramic powders may constitute a plurality of low permeability layered areas and single low permeability layered area. In the case of plural, color tone reproduce property is excellent. In the case of single, productivity is excellent and the color tone can be reproduced.

The dental zirconia blank of the present disclosure may be prepared by charging the first layer and the second layer into a mold and sintering.

The dental zirconia blank is used for the cutting and machining with CAD/CAM technique. The dental zirconia blank is provided in a state of a sintered body or in a state of a semi-sintered body. More preferably, the dental zirconia blank is provided in a state of a semi-sintered body. A dental zirconia blank provided in a state of a semi-sintered body is re-sintered after cutting and machining with CAD/CAM technique to be used in an oral cavity as a sintered body.

A shape of the dental zirconia blank may be a disk type which is a columnar shape or a block type that is a cube or a cuboid.

In the preparation of the dental zirconia blank, a coloring material may be used by mixing with the ceramic powder constituting the high permeability ceramic and the ceramic powder constituting the low permeability ceramic. It is preferable that the coloring material is solid-solved or contained in a preparation of the ceramic powder constituting the high permeability ceramic and the ceramic powder constituting the low permeability ceramic. Examples of the coloring material include an iron compound, a cobalt compound, a chromium compound, a praseodymium compound and a vanadium compound.

The ceramic powder constituting the high permeability ceramic and the ceramic powder constituting the low permeability ceramic may contain aluminum oxide as a sintering additive. It is preferable that the content of the aluminum oxide is within a range of 0.005 to 0.5 mol %. When the content of the aluminum oxide is more than 0.5 mol %, translucency may decrease and aesthetic property may be inferior in case of a front teeth.

As shown in FIG. 1, the first layer may be positioned to a position spaced from a surface of a side of the one end by a range of 5 to 40% of a dimension between the surface of the side of the one end and a surface of a side of the other end opposing to the surface of the side of the one end on a perpendicular line from the center of the gravity of the surface of the side of the one end at which the first layer (which is the enamel layer of FIG. 1) is positioned in the layering direction of the dental zirconia blank.

The first layer preferably contains a high permeability layered area containing a uniform content of yttrium oxide, a uniform content of erbium oxide and a uniform content of coloring material within a range of 50 to 100% in the first layer, and more preferably contains within a range of 50 to 100% along the perpendicular line from the center of the gravity shown in FIG. 1 in the first layer.

The second layer preferably contains a low permeability layered area containing a uniform content of yttrium oxide, a uniform content of erbium oxide and a uniform content of coloring material within a range of 50 to 100% in the second layer, and more preferably contains within a range of 50 to 100% along the perpendicular line from the center of the gravity shown in FIG. 1 in the second layer.

It is preferable that the ceramic powder constituting the high permeability ceramic and the ceramic powder constituting the low permeability ceramic have an average primary particle diameter within a range of 10 to 1000 nm and have BET specific surface area within a range of 5 to 20 $m^2/g$. When the average primary particle diameter is less than 10 nm, there are many cases where a trouble is caused in the molding. When the average primary particle diameter is more than 1000 nm, there are many cases where a trouble is caused in the molding. When the BET specific surface area is smaller than 5 $m^2/g$, there is a tendency that it is hard to sinter at low temperature. When the BET specific surface area is larger than 20 m²/g, the cohesive force is remarkable.

It is preferable that a difference of BET specific surface area between a ceramic powder constituting the high permeability ceramic and a ceramic powder constituting the low permeability ceramic is within a range of 2 m²/g. In addition, it is more preferable that the difference of BET specific surface area is within a range of 1 m²/g. Further, it is preferable that a difference of an average primary particle diameter between a ceramic powder constituting the high permeability ceramic and a ceramic powder constituting the low permeability ceramic is within a range of 20 nm. In addition, it is more preferable that the difference of the average primary particle diameter is within a range of 10 nm.

It is preferable that a difference of BET specific surface area between a powder constituting the high permeability ceramic and a powder constituting the low permeability ceramic is within a range of 2 m²/g and a difference of an average primary particle diameter between the powder constituting the high permeability ceramic and the powder constituting the low permeability ceramic is within a range of 20 nm. Further, it is more preferable that the difference of BET specific surface area is within a range of 1 m²/g and the difference of the average primary particle diameter is within a range of 10 nm.

When ceramic powders in which the difference of the BET specific surface area and the difference of the average primary particle diameter are large are layered and molded and are sintered, a strain generates in the zirconia blank molded body. Particularly, when the dental zirconia blank in a state of a semi-sintered body is cut and machined, a trouble such as a generation of a warpage due to a strain of the blank itself, a crack of a prosthesis device in final sintering and an incompatibility generates.

The BET specific surface area and the average primary particle diameter may be adjusted in a preparation of the ceramic powders constituting the high permeability ceramic and the ceramic powders constituting the low permeability ceramic.

A bending strength of the second layer of the dental zirconia blank of the present disclosure is preferably 1000 MPa or more, more preferably 1200 MPa. When the bending strength of the second layer is 1000 MPa or more, it is applicable to a frame of 4 unit or more bridge. On the other hand, a bending strength of the first layer is preferably 300 MPa or more, more preferably 700 MPa. When the bending strength of the first layer is 300 MPa or more, it is applicable to the biting force of the molar tooth. In addition, in the present specification, the bending strength means the three points bending strength according to ISO 6872.

It is preferable that the dental zirconia blank of the present disclosure consists of a plurality of high permeability layered areas and/or a plurality of low permeability layered areas. The total number of the high permeability layered areas and the low permeability layered areas is preferably within a range of 3 to 10, more preferably within a range of 4 to 6. Aesthetic property is easily provided when the high permeability layered area and/or the low permeability layered area is pluralized. However, when the total number is 11 or more, there is a tendency that productivity decreases. When the total number is within a range of 4 to 6, the dental zirconia blank is balanced with respect to aesthetic property, productivity and the like.

It is preferable that the high permeability layered area located in the surface layer has the highest transparency indicated by the contrast ratio among the high permeability layered areas contained in the dental zirconia blank.

When the chromaticities based on the L*·a*·b* colorimetric system of the first layer is expressed by LE, aE, bE, it is preferable that LE is within a range of 65.0 to 82.0, aE is within a range of −4.0 to 2.0 and bE is within a range of 0.0 to 20.0. It is more preferable that LE is within a range of 69.0 to 80.0, aE is within a range of −3.0 to 1.0 and bE is within a range of 2.0 to 15.0. Further, the chromaticities based on the L*·a*·b* colorimetric system of the at least one high permeability layered area is expressed by LE, aE, bE, it is preferable that LE is within a range of 65.0 to 82.0, aE is within a range of −4.0 to 2.0 and bE is within a range of 0.0 to 20.0. It is more preferable that LE is within a range of 69.0 to 80.0, aE is within a range of −3.0 to 1.0 and bE is within a range of 2.0 to 15.0. In addition, the transparency of the first layer and/or the transparency of the at least one high permeability layered area is higher than the transparency of the second layer. By such a constitution, the prosthesis device prepared from the zirconia blank may easily colored to reproduce the color tone close to a natural tooth.

When the chromaticities based on the L*·a*·b* colorimetric system of the second layer is expressed by LB, aB, bB, it is preferable that LB is within a range of 67.0 to 78.0, aB is within a range of −2.5 to 1.0 and bB is within a range of 5.0 to 15.0.

When the first layer does not contain a coloring material, it is preferable that a contrast ratio of the first layer of the dental zirconia blank is 0.71 or less because aesthetic property increases. On the other hand, when the first layer contains a coloring material, the contrast ratio of the first layer is within a range of 0.75 to 0.85. When the contrast ratio of the first layer containing a coloring material is less than 0.75, since permeability is too high and it becomes dark, there is a case where aesthetic property decreases. When the contrast ratio of the first layer containing a coloring material is more than 0.85, since permeability becomes too low, there is a case where permeability like a natural tooth is not exhibited.

When the second layer does not contain a coloring material, it is preferable that a contrast ratio of the second layer of the dental zirconia blank is 0.70 or more because aesthetic property increases. On the other hand, when the second layer contains a coloring material, the contrast ratio of the second layer is within a range of 0.80 to 0.90. When the contrast ratio of the second layer containing a coloring material is less than 0.80, since permeability increases, there is a case where it is easily affected by a color of an abutment tooth. When the contrast ratio of the second layer is more than 0.90, since permeability becomes too low, there is a case where it is hard to harmonize with an adjacent tooth in an oral cavity.

EXAMPLES

The present invention is described in more detail and specifically with reference to Examples. However, the present invention is not limited to Examples.

(Preparation of Ceramic Powders in Each Layer)

Commercial available zirconia powder, yttrium oxide containing zirconia powder, erbium oxide containing zirconia powder and coloring material containing zirconia powder which have an average primary particle diameter within a range of 40 to 90 nm and BET specific surface area within a range of 7 to 13 m²/g were used.

The zirconia powder, the yttrium oxide containing zirconia powder, the erbium oxide containing zirconia powder and the coloring material containing zirconia powder were used for compounding the compositions shown in Tables to prepare ceramic powders used as the first layer and the second layer. The ceramic powders were compounded with an infinitesimal coloring material of an iron compound and a cobalt compound.

(Molding Method of Dental Zirconia Blank)

Necessary amounts of each ceramic powders were filled in a metal mold having a diameter of 100 mm from the first layer side in the order described in Tables and press molding was performed by pressure of 10 kN for one minute. The shape of the test specimen is shown in FIG. 1. The upper portion of FIG. 1 corresponds to the first layer and the lower portion corresponds to the second layer.

After performing the press molding, CIP molding was performed by pressure of 200 MPa for one minute. Degreasing of the press molded body was performed by heating at 50° C./hour of temperature rising rate to 500° C., retaining for two hours and cooling at 100° C./hour of temperature drop rate to room air temperature. After degreasing, a zirconia blank which is a pre-sintered body was prepared by heating at 100° C./hour of temperature rising rate to 1000 to 1200° C., retaining for two hours and furnace cooling.

(Determine of Warp in Temporary Calcining)

The presence or absence of a warp was confirmed for the dental zirconia blank (semi-sintered body) molded by the above described method. The surface deformed in a projecting shape was set at a lower side, the distance from the setting surface to the bottom surface was measured by using the digital microscope VHX-5000 (KEYENCE CORPORATION). Ten places were measured. The rating criteria were as follow:
○: Maximum distance was 1 mm or less; and
x: Maximum distance was more than 1 mm.

(Determine of Warp in Final Calcining)

The wax up of six bridges was performed on the plaster cast in which a formation of abutment teeth of six front teeth was performed and the data of the six bridges was captured by using a scanner of D2000 (3shape A/S) and the six bridges of which the data was captured was machined from the dental zirconia blank molded by the above method. A sintered body was prepared by heating at 5° C./min of temperature rising rate to 1450° C., retaining for two hours and cooling to room air temperature and was confirmed for compatibility.

The rating criteria were as follow:
○: Compatible without no wobble when the sintered six bridges were returned to the plaster cast; and
x: Not compatible due to some wobble when the sintered six bridges were returned to the plaster cast.

(Three Point Bending Test)

A test specimen was prepared by machining a portion of 45 to 55% in the layering direction of the first layer and the second layer of the dental zirconia blank molded by the above method. A sintered body was prepared by heating at 5° C./min of temperature rising rate to 1450° C., retaining for two hours and cooling to room air temperature. The sintered body was surface polished to prepare a bending test specimen having width of 4 mm, thickness of 1.2 mm and length of 16 mm. The bending test was conducted at a distance between supporting points of 12 mm according to ISO 6872: 7.3 Flexural strength. The first layer having a bending strength of 300 MPa or more was determined to be usable in clinical. The second layer having a bending strength of 1000 MPa or more was determined to be usable in clinical.

(Measurement of Color Tone and Contrast Ratio)

A test specimen was prepared from the dental zirconia blank molded by the above method. A sintered body was prepared by heating at 5° C./min of temperature rising rate to 1450° C., retaining for two hours and cooling to room air temperature. The sintered body was surface polished to prepare a round plate having diameter of 14 mm and thickness of 1.2 mm. A chromaticity (L*, a*, b*) obtained from the color measurement over the white background was measured by using a spectral colorimeter (CM-5 manufactured by Konica Minolta, Inc.) as the color tone. In addition, the contrast ratio was calculated from the formula "the contrast ratio=1−(1−$Y_B/Y_W$)" by using the values Y measured on a white background and on a black background. In the formula, $Y_W$ is the value Y measured on a white background, and $Y_B$ is the value Y measured on a black background. When the first layer did not include the coloring material, the first layer having a contrast ratio of 0.71 or less was determined to be usable in clinical. When the first layer included the coloring material, the first layer having a contrast ratio within a range of 0.75 to 0.85 was determined to be usable in clinical. When the second layer did not include the coloring material, the second layer having a contrast ratio of 0.70 or more was determined to be usable in clinical. When the second layer included the coloring material, the second layer having a contrast ratio within a range of 0.80 to 0.90 was determined to be usable in clinical.

TABLE 1

| | | | | Amount in each layered areas | | | | | |
|---|---|---|---|---|---|---|---|---|---|
| | Order of layers | First layer or Second layer | Layer ratio (%) | Yttrium oxide content (mol %) | Erbium oxide content (mol %) | Zirconium oxide content (mol %) | Other (Aluminum oxide) (mol %) | Total | Other (Coloring material) (wt %) |
| Example 1 | 1 | First layer | 30 | 5.0000 | 0.0000 | 94.9500 | 0.0500 | 100.0000 | 0.0000 |
| | 2 | Second layer | 70 | 3.8000 | 0.0000 | 96.1500 | 0.0500 | 100.0000 | 0.0000 |
| Example 2 | 1 | First layer | 30 | 8.4000 | 0.0000 | 91.5500 | 0.0500 | 100.0000 | 0.0000 |
| | 2 | Second layer | 70 | 3.8000 | 0.0000 | 96.1500 | 0.0500 | 100.0000 | 0.0000 |
| Comparative Example 1 | 1 | First layer | 30 | 9.0000 | 0.0000 | 90.9500 | 0.0500 | 100.0000 | 0.0000 |
| | 2 | Second layer | 70 | 3.8000 | 0.0000 | 96.1500 | 0.0500 | 100.0000 | 0.0000 |
| Example 3 | 1 | First layer | 30 | 8.4000 | 0.0000 | 91.5500 | 0.0500 | 100.0000 | 0.0000 |
| | 2 | Second layer | 70 | 3.0000 | 0.0000 | 96.9500 | 0.0500 | 100.0000 | 0.0000 |
| Comparative Example 2 | 1 | First layer | 30 | 8.4000 | 0.0000 | 91.5500 | 0.0500 | 100.0000 | 0.0000 |
| | 2 | Second layer | 70 | 2.3000 | 0.0000 | 97.6500 | 0.0500 | 100.0000 | 0.0000 |
| Example 4 | 1 | First layer | 30 | 3.5000 | 0.0000 | 96.4500 | 0.0500 | 100.0000 | 0.0000 |
| | 2 | Second layer | 70 | 2.3000 | 0.0000 | 97.6500 | 0.0500 | 100.0000 | 0.0000 |

TABLE 1-continued

| | | | | Amount in each layered areas | | | | | |
|---|---|---|---|---|---|---|---|---|---|
| | Order of layers | First layer or Second layer | Layer ratio (%) | Yttrium oxide content (mol %) | Erbium oxide content (mol %) | Zirconium oxide content (mol %) | Other (Aluminum oxide) (mol %) | Total | Other (Coloring material) (wt %) |
| Comparative Example 3 | 1 | First layer | 30 | 3.0000 | 0.0000 | 96.9500 | 0.0500 | 100.0000 | 0.0000 |
| | 2 | Second layer | 70 | 2.3000 | 0.0000 | 97.6500 | 0.0500 | 100.0000 | 0.0000 |
| Example 5 | 1 | First layer | 30 | 3.5000 | 0.0000 | 96.4500 | 0.0500 | 100.0000 | 0.0000 |
| | 2 | Second layer | 70 | 3.0000 | 0.0000 | 96.9500 | 0.0500 | 100.0000 | 0.0000 |
| Comparative Example 4 | 1 | First layer | 30 | 3.8000 | 0.0000 | 96.1500 | 0.0500 | 100.0000 | 0.0000 |
| | 2 | Second layer | 70 | 3.5000 | 0.0000 | 96.4500 | 0.0500 | 100.0000 | 0.0000 |
| Example 6 | 1 | First layer | 30 | 5.0000 | 0.0000 | 94.9500 | 0.0500 | 100.0000 | 0.0000 |
| | 2 | Second layer | 70 | 4.4000 | 0.0000 | 95.5500 | 0.0500 | 100.0000 | 0.0000 |
| Comparative Example 5 | 1 | First layer | 30 | 8.4000 | 0.0000 | 91.5500 | 0.0500 | 100.0000 | 0.0000 |
| | 2 | Second layer | 70 | 5.0000 | 0.0000 | 94.9500 | 0.0500 | 100.0000 | 0.0000 |
| Example 7 | 1 | First layer | 30 | 5.0000 | 0.0000 | 94.9500 | 0.0500 | 100.0000 | 0.0000 |
| | 2 | Second layer | 70 | 1.5000 | 0.0000 | 98.4500 | 0.0500 | 100.0000 | 0.0000 |
| Comparative Example 6 | 1 | First layer | 30 | 3.5000 | 0.0000 | 96.4500 | 0.0500 | 100.0000 | 0.0000 |
| | 2 | Second layer | 70 | 1.0000 | 0.0000 | 98.9500 | 0.0500 | 100.0000 | 0.0000 |
| Example 8 | 1 | First layer | 40 | 5.0000 | 0.0000 | 94.9500 | 0.0500 | 100.0000 | 0.0000 |
| | 2 | Second layer | 60 | 3.8000 | 0.0000 | 96.1500 | 0.0500 | 100.0000 | 0.0000 |
| Example 9 | 1 | First layer | 5 | 5.0000 | 0.0000 | 94.9500 | 0.0500 | 100.0000 | 0.0000 |
| | 2 | Second layer | 95 | 3.8000 | 0.0000 | 96.1500 | 0.0500 | 100.0000 | 0.0000 |
| Example 10 | 1 | First layer | 30 | 5.0000 | 0.0001 | 94.9499 | 0.0500 | 100.0000 | 0.0000 |
| | 2 | Second layer | 70 | 3.8000 | 0.0000 | 96.1500 | 0.0500 | 100.0000 | 0.0000 |
| Example 11 | 1 | First layer | 30 | 5.0000 | 0.0000 | 94.9500 | 0.0500 | 100.0000 | 0.0000 |
| | 2 | Second layer | 70 | 3.8000 | 0.0010 | 96.1490 | 0.0500 | 100.0000 | 0.0000 |
| Example 12 | 1 | First layer | 30 | 5.0000 | 0.0100 | 94.9400 | 0.0500 | 100.0000 | 0.0000 |
| | 2 | Second layer | 70 | 3.8000 | 0.0100 | 96.1400 | 0.0500 | 100.0000 | 0.0000 |
| Example 13 | 1 | First layer | 30 | 5.0000 | 0.1000 | 94.8500 | 0.0500 | 100.0000 | 0.0000 |
| | 2 | Second layer | 70 | 3.8000 | 0.1000 | 96.0500 | 0.0500 | 100.0000 | 0.0000 |
| Example 14 | 1 | First layer | 30 | 5.0000 | 0.3000 | 94.6500 | 0.0500 | 100.0000 | 0.0000 |
| | 2 | Second layer | 70 | 3.8000 | 0.3000 | 95.8500 | 0.0500 | 100.0000 | 0.0000 |
| Example 16 | 1 | First layer | 30 | 5.0000 | 0.0000 | 94.9500 | 0.0500 | 100.0000 | 1.0000 |
| | 2 | Second layer | 70 | 3.8000 | 0.0000 | 96.1500 | 0.0500 | 100.0000 | 1.0000 |

TABLE 2

| | | | Amount in layer | | | | | |
|---|---|---|---|---|---|---|---|---|
| | First layer or Second layer | Layer ratio (%) | Yttrium oxide content (mol %) | Erbium oxide content (mol %) | Zirconium oxide content (mol %) | Other (Aluminum oxide) (mol %) | Total | Other (Coloring material) (wt %) |
| Example 1 | First layer | 30.0000 | 5.0000 | 0.0000 | 94.9500 | 0.0500 | 100.0000 | 0.0000 |
| | Second layer | 70.0000 | 3.8000 | 0.0000 | 96.1500 | 0.0500 | 100.0000 | 0.0000 |
| Example 2 | First layer | 30.0000 | 8.4000 | 0.0000 | 91.5500 | 0.0500 | 100.0000 | 0.0000 |
| | Second layer | 70.0000 | 3.8000 | 0.0000 | 96.1500 | 0.0500 | 100.0000 | 0.0000 |
| Comparative Example 1 | First layer | 30.0000 | 9.0000 | 0.0000 | 90.9500 | 0.0500 | 100.0000 | 0.0000 |
| | Second layer | 70.0000 | 3.8000 | 0.0000 | 96.1500 | 0.0500 | 100.0000 | 0.0000 |
| Example 3 | First layer | 30.0000 | 8.4000 | 0.0000 | 91.5500 | 0.0500 | 100.0000 | 0.0000 |
| | Second layer | 70.0000 | 3.0000 | 0.0000 | 96.9500 | 0.0500 | 100.0000 | 0.0000 |
| Comparative Example 2 | First layer | 30.0000 | 8.4000 | 0.0000 | 91.5500 | 0.0500 | 100.0000 | 0.0000 |
| | Second layer | 70.0000 | 2.3000 | 0.0000 | 97.6500 | 0.0500 | 100.0000 | 0.0000 |
| Example 4 | First layer | 30.0000 | 3.5000 | 0.0000 | 96.4500 | 0.0500 | 100.0000 | 0.0000 |
| | Second layer | 70.0000 | 2.3000 | 0.0000 | 97.6500 | 0.0500 | 100.0000 | 0.0000 |
| Comparative Example 3 | First layer | 30.0000 | 3.0000 | 0.0000 | 96.9500 | 0.0500 | 100.0000 | 0.0000 |
| | Second layer | 70.0000 | 2.3000 | 0.0000 | 97.6500 | 0.0500 | 100.0000 | 0.0000 |
| Example 5 | First layer | 30.0000 | 3.5000 | 0.0000 | 96.4500 | 0.0500 | 100.0000 | 0.0000 |
| | Second layer | 70.0000 | 3.0000 | 0.0000 | 96.9500 | 0.0500 | 100.0000 | 0.0000 |
| Comparative Example 4 | First layer | 30.0000 | 3.8000 | 0.0000 | 96.1500 | 0.0500 | 100.0000 | 0.0000 |
| | Second layer | 70.0000 | 3.5000 | 0.0000 | 96.4500 | 0.0500 | 100.0000 | 0.0000 |
| Example 6 | First layer | 30.0000 | 5.0000 | 0.0000 | 94.9500 | 0.0500 | 100.0000 | 0.0000 |
| | Second layer | 70.0000 | 4.4000 | 0.0000 | 95.5500 | 0.0500 | 100.0000 | 0.0000 |
| Comparative Example 5 | First layer | 30.0000 | 8.4000 | 0.0000 | 91.5500 | 0.0500 | 100.0000 | 0.0000 |
| | Second layer | 70.0000 | 5.0000 | 0.0000 | 94.9500 | 0.0500 | 100.0000 | 0.0000 |
| Example 7 | First layer | 30.0000 | 5.0000 | 0.0000 | 94.9500 | 0.0500 | 100.0000 | 0.0000 |
| | Second layer | 70.0000 | 1.5000 | 0.0000 | 98.4500 | 0.0500 | 100.0000 | 0.0000 |
| Comparative Example 6 | First layer | 30.0000 | 3.5000 | 0.0000 | 96.4500 | 0.0500 | 100.0000 | 0.0000 |
| | Second layer | 70.0000 | 1.0000 | 0.0000 | 98.9500 | 0.0500 | 100.0000 | 0.0000 |
| Example 8 | First layer | 40.0000 | 5.0000 | 0.0000 | 94.9500 | 0.0500 | 100.0000 | 0.0000 |
| | Second layer | 60.0000 | 3.8000 | 0.0000 | 96.1500 | 0.0500 | 100.0000 | 0.0000 |

TABLE 2-continued

| | First layer or Second layer | Layer ratio (%) | Yttrium oxide content (mol %) | Erbium oxide content (mol %) | Zirconium oxide content (mol %) | Other (Aluminum oxide) (mol %) | Total | Other (Coloring material) (wt %) |
|---|---|---|---|---|---|---|---|---|
| Example 9 | First layer | 40.0000 | 5.0000 | 0.0000 | 94.9500 | 0.0500 | 100.0000 | 0.0000 |
| | Second layer | 60.0000 | 3.8000 | 0.0000 | 96.1500 | 0.0500 | 100.0000 | 0.0000 |
| Example 10 | First layer | 30.0000 | 5.0000 | 0.0001 | 94.9499 | 0.0500 | 100.0000 | 0.0000 |
| | Second layer | 70.0000 | 3.8000 | 0.0000 | 96.1500 | 0.0500 | 100.0000 | 0.0000 |
| Example 11 | First layer | 30.0000 | 5.0000 | 0.0000 | 94.9500 | 0.0500 | 100.0000 | 0.0000 |
| | Second layer | 70.0000 | 3.8000 | 0.0010 | 96.1490 | 0.0500 | 100.0000 | 0.0000 |
| Example 12 | First layer | 30.0000 | 5.0000 | 0.0100 | 94.9400 | 0.0500 | 100.0000 | 0.0000 |
| | Second layer | 70.0000 | 3.8000 | 0.0100 | 96.1400 | 0.0500 | 100.0000 | 0.0000 |
| Example 13 | First layer | 30.0000 | 5.0000 | 0.1000 | 94.8500 | 0.0500 | 100.0000 | 0.0000 |
| | Second layer | 70.0000 | 3.8000 | 0.1000 | 96.0500 | 0.0500 | 100.0000 | 0.0000 |
| Example 14 | First layer | 30.0000 | 5.0000 | 0.3000 | 94.6500 | 0.0500 | 100.0000 | 0.0000 |
| | Second layer | 70.0000 | 3.8000 | 0.3000 | 95.8500 | 0.0500 | 100.0000 | 0.0000 |
| Example 16 | First layer | 30.0000 | 5.0000 | 0.0000 | 94.9500 | 0.0500 | 100.0000 | 1.0000 |
| | Second layer | 70.0000 | 3.8000 | 0.0000 | 96.1500 | 0.0500 | 100.0000 | 1.0000 |

TABLE 3

| | First layer or Second layer | physical property in each layers | | | | | | Test results | | |
|---|---|---|---|---|---|---|---|---|---|---|
| | | BET specific surface area (m2/g) | Average primary particle diameter (nm) | L* | a* | b* | Contrast ratio | Warp in temporary calcining | Warp in final calcining | Three point bending test (Mpa) |
| Example 1 | First layer | 10.0 | 89.5 | 83.4 | −0.8 | −3.0 | 0.68 | ○ | ○ | 900 |
| | Second layer | 10.2 | 87.0 | 87.0 | −0.9 | −2.1 | 0.71 | | | 1340 |
| Example 2 | First layer | 9.8 | 100.0 | 74.2 | −0.7 | −3.2 | 0.62 | ○ | ○ | 310 |
| | Second layer | 10.2 | 87.0 | 87.0 | −0.9 | −2.1 | 0.71 | | | 1340 |
| Comparative Example 1 | First layer | 8.0 | 91.0 | 72.8 | −0.7 | −3.3 | 0.60 | ○ | ○ | 250 |
| | Second layer | 10.2 | 87.0 | 87.0 | −0.9 | −2.1 | 0.71 | | | 1340 |
| Example 3 | First layer | 9.8 | 100.0 | 74.2 | −0.7 | −3.2 | 0.62 | ○ | ○ | 310 |
| | Second layer | 9.3 | 86.0 | 89.3 | −0.9 | −1.9 | 0.72 | | | 1400 |
| Comparative Example 2 | First layer | 9.8 | 100.0 | 74.2 | −0.7 | −3.2 | 0.62 | × | × | 310 |
| | Second layer | 9.7 | 66.8 | 91.4 | −0.9 | −2.0 | 0.74 | | | 1430 |
| Example 4 | First layer | 8.5 | 85.0 | 87.8 | −0.9 | −2.0 | 0.71 | ○ | ○ | 1360 |
| | Second layer | 9.7 | 66.8 | 91.4 | −0.9 | −2.0 | 0.74 | | | 1430 |
| Comparative Example 3 | First layer | 9.3 | 86.0 | 89.3 | −0.9 | −1.9 | 0.72 | ○ | ○ | 1400 |
| | Second layer | 9.7 | 66.8 | 91.4 | −0.9 | −2.0 | 0.74 | | | 1430 |
| Example 5 | First layer | 8.5 | 85.0 | 87.8 | −0.9 | −2.0 | 0.71 | ○ | ○ | 1360 |
| | Second layer | 9.3 | 86.0 | 89.3 | −0.9 | −1.9 | 0.72 | | | 1400 |
| Comparative Example 4 | First layer | 10.2 | 87.0 | 87.0 | −0.9 | −2.1 | 0.71 | ○ | ○ | 1340 |
| | Second layer | 8.5 | 85.0 | 87.8 | −0.9 | −2.0 | 0.71 | | | 1360 |
| Example 6 | First layer | 10.0 | 89.5 | 83.4 | −0.8 | −3.0 | 0.68 | ○ | ○ | 900 |
| | Second layer | 10.1 | 89.0 | 86.3 | −0.9 | −2.4 | 0.70 | | | 1250 |
| Comparative Example 5 | First layer | 9.8 | 100.0 | 74.2 | −0.7 | −3.2 | 0.62 | ○ | ○ | 310 |
| | Second layer | 10.0 | 89.5 | 83.4 | −0.8 | −3.0 | 0.68 | | | 900 |
| Example 7 | First layer | 10.0 | 89.5 | 83.4 | −0.8 | −3.0 | 0.68 | ○ | ○ | 900 |
| | Second layer | 10.0 | 100.0 | 93.7 | −1.0 | −1.4 | 0.75 | | | 1100 |
| Comparative Example 6 | First layer | 8.5 | 85.0 | Difficult to preparation (sintered body collapsed) | | | | | | |
| | Second layer | 13.0 | 40.0 | | | | | | | |
| Example 8 | First layer | 10.0 | 89.5 | 83.4 | −0.8 | −3.0 | 0.68 | ○ | ○ | 900 |
| | Second layer | 10.2 | 87.0 | 87.0 | −0.9 | −2.1 | 0.71 | | | 1340 |
| Example 9 | First layer | 10.0 | 89.5 | 83.4 | −0.8 | −3.0 | 0.68 | ○ | ○ | 900 |
| | Second layer | 10.2 | 87.0 | 87.0 | −0.9 | −2.1 | 0.71 | | | 1340 |
| Example 10 | First layer | 10.0 | 89.5 | 83.1 | −0.7 | −3.1 | 0.68 | ○ | ○ | 900 |
| | Second layer | 10.2 | 87.0 | 87.0 | −0.9 | −2.1 | 0.71 | | | 1340 |
| Example 11 | First layer | 10.0 | 89.5 | 83.4 | −0.8 | −3.0 | 0.68 | ○ | ○ | 900 |
| | Second layer | 10.2 | 87.0 | 86.7 | −0.3 | −3.7 | 0.71 | | | 1340 |
| Example 12 | First layer | 10.0 | 89.5 | 82.5 | 1.0 | −3.6 | 0.69 | ○ | ○ | 890 |
| | Second layer | 10.2 | 87.0 | 86.0 | 1.2 | −3.9 | 0.72 | | | 1330 |
| Example 13 | First layer | 10.0 | 89.5 | 81.9 | 6.1 | −4.1 | 0.70 | ○ | ○ | 890 |
| | Second layer | 10.2 | 87.0 | 85.1 | 6.7 | −4.0 | 0.74 | | | 1330 |
| Example 14 | First layer | 10.1 | 89.0 | 81.3 | 8.1 | −4.7 | 0.71 | ○ | ○ | 880 |
| | Second layer | 10.2 | 87.0 | 84.5 | 8.8 | −4.2 | 0.75 | | | 1310 |
| Example 16 | First layer | 10.0 | 89.5 | 79.4 | −3.0 | 9.2 | 0.75 | ○ | ○ | 890 |
| | Second layer | 10.2 | 87.0 | 80.5 | −2.3 | 11.5 | 0.80 | | | 1320 |

TABLE 4

| | Order of layers | First layer or Second layer | Layer ratio (%) | Amount in each layered areas | | | | | Other (Coloring material) (wt %) |
|---|---|---|---|---|---|---|---|---|---|
| | | | | Yttrium oxide content (mol %) | Erbium oxide content (mol %) | Zirconium oxide content (mol %) | Other (Aluminum oxide) (mol %) | Total | |
| Example 17 | 1 | First layer | 15 | 8.40000 | 0.00000 | 91.55000 | 0.05000 | 100.00000 | 0.00000 |
| | 2 | | 15 | 5.00000 | 0.00000 | 94.95000 | 0.05000 | 100.00000 | 0.00000 |
| | 3 | Second layer | 70 | 3.80000 | 0.00000 | 96.15000 | 0.05000 | 100.00000 | 0.00000 |
| Example 18 | 1 | First layer | 30 | 5.00000 | 0.00000 | 94.95000 | 0.05000 | 100.00000 | 0.00000 |
| | 2 | Second layer | 35 | 3.80000 | 0.00000 | 96.15000 | 0.05000 | 100.00000 | 0.00000 |
| | 3 | layer | 35 | 3.00000 | 0.00000 | 96.95000 | 0.05000 | 100.00000 | 0.00000 |
| Example 19 | 1 | First layer | 15 | 8.40000 | 0.00000 | 91.55000 | 0.05000 | 100.00000 | 0.00000 |
| | 2 | | 15 | 5.00000 | 0.00000 | 94.95000 | 0.05000 | 100.00000 | 0.00000 |
| | 3 | Second layer | 35 | 3.80000 | 0.00000 | 96.15000 | 0.05000 | 100.00000 | 0.00000 |
| | 4 | layer | 35 | 3.00000 | 0.00000 | 96.95000 | 0.05000 | 100.00000 | 0.00000 |
| Example 20 | 1 | First layer | 15 | 8.40000 | 0.00000 | 91.55000 | 0.05000 | 100.00000 | 0.00000 |
| | 2 | | 15 | 5.0000 | 0.1000 | 94.8500 | 0.05000 | 100.00000 | 0.0000 |
| | 3 | Second layer | 35 | 3.8000 | 0.1000 | 96.0500 | 0.05000 | 100.00000 | 0.0000 |
| | 4 | | 35 | 3.00000 | 0.00000 | 96.95000 | 0.05000 | 100.00000 | 0.00000 |

TABLE 5

| | First layer or Second layer | Layer ratio (%) | Yttrium oxide content (mol %) | Erbium oxide content (mol %) | Zirconium oxide content (mol %) | Other (Aluminum oxide) (mol %) | Total | Other (Coloring material) (wt %) |
|---|---|---|---|---|---|---|---|---|
| Example 17 | First layer | 30.00000 | 6.70000 | 0.00000 | 93.25000 | 0.05000 | 100.00000 | 0.00000 |
| | Second layer | 70.00000 | 3.80000 | 0.00000 | 96.15000 | 0.05000 | 100.00000 | 0.00000 |
| Example 18 | First layer | 30.00000 | 5.00000 | 0.00000 | 94.95000 | 0.05000 | 100.00000 | 0.00000 |
| | Second layer | 70.00000 | 3.40000 | 0.00000 | 96.55000 | 0.05000 | 100.00000 | 0.00000 |
| Example 19 | First layer | 30.00000 | 6.70000 | 0.00000 | 93.25000 | 0.05000 | 100.00000 | 0.00000 |
| | Second layer | 70.00000 | 3.40000 | 0.00000 | 96.55000 | 0.05000 | 100.00000 | 0.00000 |
| Example 20 | First layer | 30.00000 | 6.70000 | 0.05000 | 93.20000 | 0.05000 | 100.00000 | 0.00000 |
| | Second layer | 70.00000 | 3.40000 | 0.05000 | 96.50000 | 0.05000 | 100.00000 | 0.00000 |

TABLE 6

| | First layer or Second layer | BET specific surface area (m2/g) | Average primary particle diameter (nm) | $L^*$ | $a^*$ | $b^*$ | Contrast ratio | Warp in temporary calcining | Warp in final calcining | Three point bending test (Mpa) |
|---|---|---|---|---|---|---|---|---|---|---|
| Example 17 | First layer | 9.9 | 94.8 | 78.8 | −0.8 | −3.1 | 0.65 | ○ | ○ | 1210 |
| | Second layer | 10.2 | 87.0 | 87.0 | −0.9 | −2.1 | 0.71 | | | 1340 |
| Example 18 | First layer | 10.0 | 89.5 | 83.4 | −0.8 | −3.0 | 0.68 | ○ | ○ | 900 |
| | Second layer | 9.8 | 86.5 | 88.2 | −0.9 | −2.0 | 0.72 | | | 1370 |
| Example 19 | First layer | 9.9 | 94.8 | 78.8 | −0.8 | −3.1 | 0.65 | ○ | ○ | 610 |
| | Second layer | 9.8 | 86.5 | 88.2 | −0.9 | −2.0 | 0.72 | | | 1370 |
| Example 20 | First layer | 9.9 | 94.8 | 78.1 | 2.7 | −3.7 | 0.66 | ○ | ○ | 600 |
| | Second layer | 9.8 | 86.5 | 87.2 | 2.9 | −3.0 | 0.73 | | | 1370 |

In the examples 1 to 20, a warpage caused in semi-sintering was 1 mm or less, there was no wobble caused in final sintering and the compatibility was good. In addition, the 3 points bending strength of the test specimen prepared from an intermediate layer (positioned in 45 to 55% from the surface of the first layer) of the zirconia blank was 1000 MPa or more. Further, the contrast ratio of the first layer was 0.71 or less, the contrast ratio of the second layer was 0.70 or more and the first layer and the second layer satisfied the relationship first layer contrast ratio<second layer contrast ratio, therefore, sufficient aesthetic property was exhibited.

In the comparative Example 1, the bending strength of the first layer was insufficient.

In the comparative Example 2, a warpage caused in semi-sintering was more than 1 mm and there was a wobble caused in final sintering and the compatibility was not good.

In the comparative Example 3, the contrast ratio of the first layer was high and sufficient aesthetic property was not obtained.

In the comparative Example 4, there was no difference in the contrast ratio between the first layer and the second layer and sufficient aesthetic property was not obtained.

In the comparative Example 5, the contrast ratio of the second layer was low and sufficient aesthetic property was not obtained.

In the comparative Example 6, the sintered body collapsed and it was impossible to perform the tests.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present disclosure provides a zirconia prosthesis device which can be cut and machined with CAD/CAM technique and exhibits high permeability and high strength after sintering. It is possible to use in various clinical case because applicable clinical case is not limited and to reproduce a color tone near to a natural tooth by multicolor multilayer structure.

DESCRIPTION OF REFERENCE NUMERAL

1: First layer (enamel layer)
2: Second layer (body layer)

What is claimed is:
1. A dental zirconia blank consisting of;
a first layer consisting of a high permeability ceramic containing 91.6 to 96.5 mol % of zirconium oxide and 3.5 to 8.4 mol % of yttrium oxide, and
a second layer consisting of a low permeability ceramic containing 95.6 to 98.5 mol % of zirconium oxide and 1.5 to 4.4 mol % of yttrium oxide, wherein
a content rate of yttrium oxide in the low permeability ceramic is lower than a content rate of yttrium oxide in the high permeability ceramic by 0.5 to 5.4 mol %,
a ceramic powder constituting the high permeability ceramic and a ceramic powder constituting the low permeability ceramic have BET specific surface areas within a range of 5 to 20 $m^2/g$, and
the ceramic powder constituting the high permeability ceramic and the ceramic powder constituting the low permeability ceramic have average primary particle diameters within a range of 10 to 1000nm.
2. The dental zirconia blank according to claim 1, wherein the first layer consists of a plurality of high permeability layered areas having different compositions with each other.

3. The dental zirconia blank according to claim 2, wherein the first layer consists of a plurality of high permeability layered areas having different content rates of zirconium oxide and/or different content rates of yttrium oxide in the high permeability ceramic with each other.
4. The dental zirconia blank according to claim 2, wherein at least one high permeability layered area includes 0.0001 to 0.30 mol % of erbium oxide.
5. The dental zirconia blank according to claim 1, wherein the second layer consists of a plurality of low permeability layered areas having different compositions with each other.
6. The dental zirconia blank according to claim 5, wherein the second layer consists of a plurality of low permeability layered areas having different content rates of zirconium oxide and/or different content rates of yttrium oxide in the low permeability ceramic with each other.
7. The dental zirconia blank according to claim 5, wherein at least one low permeability layered area includes 0.0001 to 0.30 mol % of erbium oxide.
8. The dental zirconia blank according to claim 1, wherein the high permeability ceramic is a temporary calcined body of a plurality of powders having different compositions with each other.
9. The dental zirconia blank according to claim 1, wherein the low permeability ceramic is a temporary calcined body of a plurality of powders having different compositions with each other.
10. The dental zirconia blank according to claim 1, wherein
the first layer is positioned to a position spaced from a surface of a side of one end in a layering direction by a range of 5 to 40% of a dimension between the surface of the side of the one end and a surface of a side of the other end opposing to the surface of the side of the one end on a perpendicular line from the center of the gravity of the surface of the side of the one end at which the first layer is positioned in the layering direction of the dental zirconia blank.
11. The dental zirconia blank according to claim 1, wherein
a difference of BET specific surface area between the ceramic powder constituting the high permeability ceramic and the ceramic powder constituting the low permeability ceramic is within a range of 2 $m^2/g$ and a difference of an average primary particle diameter between the ceramic powder constituting the high permeability ceramic and the ceramic powder constituting the low permeability ceramic is within a range of 20 nm.
12. The dental zirconia blank according to claim 2, wherein
transparency of at least one high permeability layered area is higher than transparency of the second layer, and
the chromaticities LE, aE, bE of the at least one high permeability layered area based on the L*·a*·b* colorimetric system satisfy the following relations:

$$65.0 \le LE \le 82.0$$

$$-4.0 \le aE \le 2.0$$

$$0.0 \le bE \le 20.0.$$

13. The dental zirconia blank according to claim 1, wherein
transparency of the first layer is higher than transparency of the second layer, and the chromaticities LE, aE, bE of the first layer based on the L*·a*·b* colorimetric system satisfy the following relations:

$$65.0 \leq LE \leq 82.0$$

$$-4.0 \leq aE \leq 2.0$$

$$0.0 \leq bE \leq 20.0.$$

14. The dental zirconia blank according to claim 1, wherein
the high permeability ceramic includes 0.0001 to 0.30 mol % of erbium oxide.

15. The dental zirconia blank according to claim 1, wherein
the low permeability ceramic includes 0.0001 to 0.30 mol % of erbium oxide.

16. The dental zirconia blank according to claim 1, wherein
the first layer consists of a plurality of high permeability layered areas having different compositions with each other, and
the second layer consists of a plurality of low permeability layered areas having different compositions with each other.

17. The dental zirconia blank according to claim 1, wherein
the first layer consists of a plurality of high permeability layered areas having different content rates of zirconium oxide and/or different content rates of yttrium oxide in the high permeability ceramic with each other, and
the second layer consists of a plurality of low permeability layered areas having different content rates of zirconium oxide and/or different content rates of yttrium oxide in the low permeability ceramic with each other.

* * * * *